(12) United States Patent
Wang et al.

(10) Patent No.: US 9,149,537 B2
(45) Date of Patent: Oct. 6, 2015

(54) COMPOSITIONS AND METHODS FOR THE TREATMENT OF TRAUMATIC BRAIN INJURY

(75) Inventors: Dong Wang, Omaha, NE (US); Matthew Kelso, Papillion, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 13/880,829

(22) PCT Filed: Nov. 4, 2011

(86) PCT No.: PCT/US2011/059308
§ 371 (c)(1),
(2), (4) Date: May 28, 2013

(87) PCT Pub. No.: WO2012/061695
PCT Pub. Date: May 10, 2012

(65) Prior Publication Data
US 2013/0243696 A1  Sep. 19, 2013

Related U.S. Application Data

(60) Provisional application No. 61/410,213, filed on Nov. 4, 2010.

(51) Int. Cl.
*A61K 8/00* (2006.01)
*A61K 47/48* (2006.01)
*A61K 45/06* (2006.01)
*A61K 49/00* (2006.01)

(52) U.S. Cl.
CPC ........... *A61K 47/48176* (2013.01); *A61K 45/06* (2013.01); *A61K 49/00* (2013.01); *A61K 49/0008* (2013.01); *A61K 47/48* (2013.01); *A61K 47/48007* (2013.01); *A61K 47/48023* (2013.01); *A61K 47/48169* (2013.01); *A61K 47/48192* (2013.01)

(58) Field of Classification Search
None
See application file for complete search history.

(56) References Cited

U.S. PATENT DOCUMENTS

| | | | |
|---|---|---|---|
| 8,168,222 B2 | 5/2012 | Kabanov et al. | |
| 2008/0044463 A1* | 2/2008 | Shaw et al. | 424/450 |
| 2008/0159959 A1 | 7/2008 | Wang et al. | |
| 2009/0311182 A1 | 12/2009 | Wang et al. | |
| 2010/0291065 A1 | 11/2010 | Kabanov et al. | |
| 2012/0189543 A1 | 7/2012 | Wang et al. | |

OTHER PUBLICATIONS

Faupel et al. "Dexamethasone in Severe Head Injuries", Neurosurg. Rev. 2 (1979) 105-111.*
Vicent, M.J., et al. "Polymer-Drug Conjugates as Modulators of Cellular Apoptosis." AAPS Journal. 2007;9(2):E200-E207.
Braakman, R., et al. "Megadose steroids in severe head injury. Results of a prospective double-blind clinical trial." J Neurosurg. Mar. 1983;58(3):326-30. [Abstract].
Krakovicova, H., et al. "HPMA-based polymer conjugates with drug combination." Eur J Pharm Sci. 2009;37:405-412.
Liu et al., "Synthesis and Evaluation of a Well-Defined HPMA Copolymer-Dexamethasone Conjugate for Effective Treatment of Rheumatoid Arthritis," Pharm. Res. (2008) 25:2910-9.
Quan et al., "Development of Macromolecular Prodrug for Treatment of Inflammatory Arthritis: Mechanisms Involved in Arthrotropism and Sustained Therapeutic Efficacy," Arthritis Res. Ther. (2010) 12:R170.

* cited by examiner

*Primary Examiner* — James Rogers
(74) *Attorney, Agent, or Firm* — Robert C. Netter, Jr.; Kathleen D. Rigaut; Dann, Dorfman, Herrell & Skillman

(57) ABSTRACT

Compositions and methods for the inhibition and/or prevention of traumatic brain injury and the symptoms associated with it are provided.

8 Claims, 5 Drawing Sheets

COMPOSITIONS AND METHODS FOR THE TREATMENT OF TRAUMATIC BRAIN INJURY

This application is a §371 application of PCT/US2011/059308, filed Nov. 4, 2011, which claims priority under 35 U.S.C. §119(e) to U.S. Provisional Patent Application No. 61/410,213, filed on Nov. 4, 2010. The foregoing applications are incorporated by reference herein.

This invention was made with government support under Grant No. 1R01 AR053325 awarded by the National Institutes of Health. The government has certain rights in the invention.

FIELD OF THE INVENTION

This invention relates to traumatic brain injury and methods of inhibiting and/or preventing the symptoms associated with the injury.

BACKGROUND OF THE INVENTION

Several publications and patent documents are cited throughout the specification in order to describe the state of the art to which this invention pertains. Each of these citations is incorporated herein by reference as though set forth in full.

Nearly 30% of all patients with combat-related injuries returning from the current conflicts in Iraq and Afghanistan sustained a traumatic brain injury (TBI), causing significant personal, social and economical impact to the country. The processes leading to neurodegeneration happen early and are irreversible, which makes the battlefield emergency treatment critical for patient brain function preservation and recovery. In addition to the military injuries, there are currently an estimated 1.7 million civilian cases of TBI annually. However, at present, no treatment for TBI is available as the brain is difficult to access with therapeutic agents due to the presence of the brain blood barrier (BBB).

SUMMARY OF THE INVENTION

In accordance with the instant invention, methods of inhibiting, reducing, and/preventing the pathology associated with traumatic injury to the brain are provided. In a particular embodiment, the method comprises administering to the subject at least one polymer, particularly a N-(2-hydroxypropyl)methacrylamide (HPMA) copolymer, conjugated to at least one anti-inflammatory agent. The anti-inflammatory agent may be conjugated to the HPMA copolymer via a linker, such as a cleavable linker or a pH sensitive linker (e.g., a linker comprising a hydrazone). In a particular embodiment, the anti-inflammatory agent is dexamethasone, tirilazad, cyclosporine, progesterone, U-83836E or pharmaceutically acceptable salts thereof. In a particular embodiment, the copolymers of the instant invention are administered to the subject soon or immediately after the traumatic brain injury. In a particular embodiment of the instant invention, the copolymer further comprises at least one imaging agent.

In accordance with another aspect of the instant invention, methods of imaging a traumatic brain injury (e.g., the lesions) in a subject are provided. In a particular embodiment, the method comprises administering to the subject at least one copolymer, particularly a N-(2-hydroxypropyl)methacrylamide (HPMA) copolymer, conjugated to at least one imaging agent and detecting the location of the imaging agent.

DETAILED DESCRIPTION OF THE INVENTION

Figure 1:
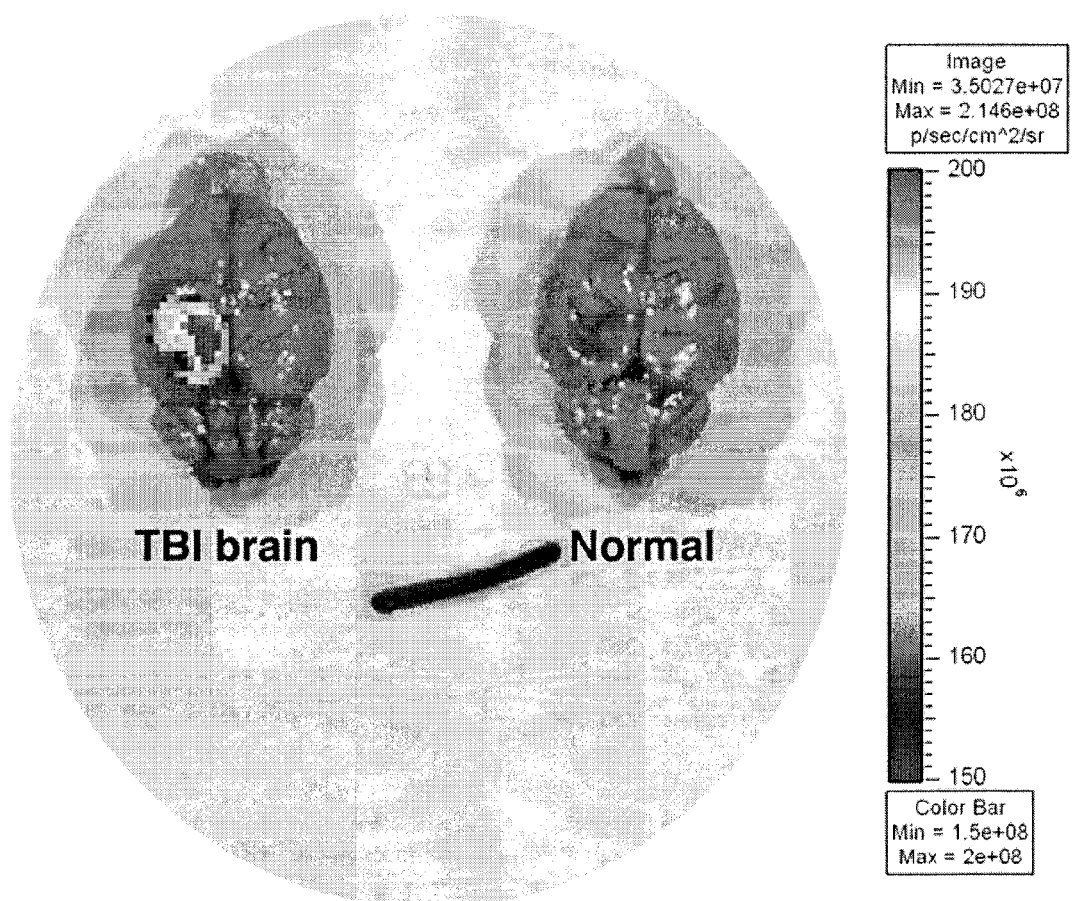
FIG. 1 provides images of brains from control rats or rats given a traumatic brain injury (TBI), after administration of near infrared dye labeled HPMA copolymers.

Herein, a novel anti-inflammation macromolecular platform (prodrug) is provided as a therapy that targets trauma lesions in the brain and provides neuroprotection to the subject. Indeed, it is demonstrated herein that a macromolecular platform based on N-(2-hydroxypropyl)methacrylamide (HPMA) copolymers is able to deliver conjugated therapeutic agents (e.g., anti-inflammatories) to the brain after TBI. Without being bound by theory, it appears that under pathological conditions such as TBI, the blood brain barrier is impaired sufficiently to allow macromolecules to infiltrate and accumulate at the lesions created by the TBI. The unexpected targeting of the HPMA copolymers to the brain, more specifically TBI-induced lesions, allows for superior delivery of therapeutic agents conjugated to the polymer. Indeed, unlike the unconjugated low molecular weight parent drugs, the prodrugs of the instant invention target the TBI sites and are retained at the site for gradual processing and drug release. This will control the local inflammation and provide effective neuroprotection.

In a particular embodiment, the copolymers of the instant invention comprise at least one therapeutic agent, particularly a therapeutic agent for the treatment of TBI. Notably, certain inflammatory cells such as microglia are abundant at the brain injury sites after TBI. $O_2$ stress and acidosis are also known to associate with the TBI. Accordingly, in a particular embodiment of the instant invention, at least one anti-inflammatory agent is conjugated to the HPMA copolymer for treating TBI. Anti-inflammatory therapeutic agents include compounds for the treatment of an inflammatory disease or the symptoms associated therewith. Anti-inflammatory therapeutic agents are provided, for example, in Goodman & Gilman's The Pharmacological Basis of Therapeutics, $12^{th}$ ed., Brunton et al., eds., McGraw-Hill Press (2010) and Remington: The Science and Practice of Pharmacy, 21th ed. Lippincott Williams & Wilkins (2005). Examples of anti-inflammatories include, without limitation: 1) steroidal anti-inflammatories such as, without limitation, glucocorticoids, corticosteroids, hydrocortisone, tirilazad (e.g., tirilazad mesylate), lazaroids (e.g., U-83836E), hydroxyltriamcinolone, progesterone, alpha-methyl dexamethasone, dexamethasone-phosphate, beclomethasone dipropionate, clobetasol valerate, desonide, desoxycorticosterone acetate, dexamethoasone, dexamethasone palmitate, dichlorisone, deflorasonediacetate, diflucortolone valerate, fluadronolone, fluclarolone acetonide, fludrocortisone, flumethasone pivalate, fluosinolone acetonide, fluocionide, flucortine butylester, fluocortolone, flupredidene (flupredylidene) acetate, flurandronolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone acetate, clocortelone, budesonide, clescinolone, dichlorisone, diflupredisone, flucloronide, flunisolide, fluoromethalone, fluperolone, fluprednisolone, hydrocortisone valerate, fluticasone, hydrocortisone cyclopentylpropionate, hydrocortamate, meprednisone, paramethasone, prednisolone, prednisone, beclomethasone dipropionate, triamcinolone, and esters and pharmaceutically acceptable salts thereof; and 2) non-steroidal anti-inflammatory agents (NSAIDs) such as, without limitation salicylates (e.g., aspirin (acetylsalicylic acid), diflunisal, salsalate), acetic acid derivatives (e.g., indomethacin, sulindac, etodolac, ketorolac, diclofenac, nabumetone), fenamic acid derivatives (fenamates) (e.g., mefenamic acid, meclofenamic acid, flufenamic acid, tolfenamic acid), propionic acid derivatives (e.g., ibuprofen, naproxen, fenoprofen, ketoprofen, flurbiprofen, oxaprozin, loxoprofen), enolic acid (oxicams) derivatives (e.g., piroxicam, meloxicam, tenoxicam, droxicam, lornoxicam, isoxicam), COX-2 inhibitors (Coxibs) (e.g., celecoxib), pyrazoles, and pharmaceutically acceptable salts thereof. In a particular embodiment, the anti-inflammatory is dexamethasone, tirilazad, cyclosporine, progesterone, U-83836E, or pharmaceutically acceptable salts thereof.

In a particular embodiment, the copolymer of the instant invention may be conjugated with at least one imaging agent. Such copolymers are useful for non-invasive imaging, diagnosis, and evaluation of TBI and may also be used to monitor the progress of a treatment. In a particular embodiment, one or more imaging agents may be combined with one or more therapeutic agents, to produce a drug/imaging agent combination, which, for example, may be used to treat and/or monitor the subject. Examples of imaging agents include, without limitation, optical imaging agents (e.g., near IR dyes (e.g., IRDye 800CW) phorphyrins, anthraquinones, anthrapyrazoles, perylenequinones, xanthenes, cyanines, acridines, phenoxazines, phenothiazines and derivatives thereof), fluorescent compounds (e.g., Alexa Fluor® 488, fluorescein, rhodamine, DiI, DiO, and derivatives thereof), chromophores, paramagnetic or superparamagnetic ions (e.g., Gd(III), Eu(III), Dy(III), Pr(III), Pa(IV), Mn(II), Cr(III), Co(III), Fe(III), Cu(II), Ni(II), Ti(III), and V(IV)), magnetic resonance imaging (MRI) contrast agents (for example, DOTA-Gd$^{3+}$, DTPA-Gd$^{3+}$ (gadolinium complex with diethylenetriamine pentaacetic acid)), positron emission tomography (PET) agents (labeled or complexed with $^{11}$C, $^{13}$N, $^{15}$O, $^{18}$F, $^{64}$Cu, $^{68}$Ga, or $^{82}$Rb (e.g., $^{18}$F-FDG (fluorodeoxyglucose))), computerized tomography (CT) agents (for example, iodine or barium containing compounds, e.g., 2,3,5-triiodobenzoic acid), gamma or positron emitters (for example, 99mTc, 111In, 113In, 153Sm, 123I, 131I 18F, 64Cu, 201Tl, etc., optionally complexed to other compounds), radioisotopes, isotopes, biotin, gold (e.g., nanoparticles), and the like. The average mol percentage of imaging agent per polymer chain may range from 0% to about 50%. One exemplary embodiment of a drug/imaging agent is a method of determining the effects of a particular drug or drug combination. For example, the drug/imaging agent may contain a candidate drug wherein the imaging agent allows for enhanced monitoring of the candidate drugs effects. In another exemplary embodiment, the drug/imaging agent may also be used to treat a subject and to monitor the subject's response to the treatment.

The therapeutic agent(s) (or imaging agent) may be conjugated to the HPMA copolymers directly (e.g., a bond) or via a linker. The linker may be non-degradable or degradable under physiological conditions. In a particular embodiment, the imaging agent is conjugated via a non-degradable linker. In a particular embodiment, the therapeutic agent is conjugated via an environmentally cleavable linker (degradable under physiological conditions). For example, the linker may be cleaved upon a stimulus including, but not limited to, changes in pH (e.g., acid labile), presence of a specific enzyme activity (for example, cathepsins (e.g., cathepsin K), MMPs, and the like), changes in oxygen levels, and the like. In certain embodiments, the linker is an aryl or alkyl having from one to about 50 carbons, particularly one to about 15 carbons. In certain embodiments, the linker is a peptide (e.g., natural amino acids) having from 1 to about 20, particularly 1 to about 10 residues. In certain embodiment, the linker is pH sensitive, particularly wherein the bond is cleaved under acidic conditions (e.g., pH<6, particularly <5.5). In a particular embodiment, the linker comprises at least one hydrazone bond, acetal bond, cis-aconityl spacer, phosphamide bond, and/or silyl ether bond. In a particular embodiment, the linker comprises a pH sensitive hydrazone bond.

As used herein, "traumatic brain injury" or "TBI" refers to an acquired brain injury or a head injury, when a trauma causes damage to the brain. Trauma includes, e.g., post-head trauma, impact trauma, and other traumas to the head such as, for example, traumas caused by accidents and/or sports injuries, concussive injuries, penetrating head wounds, brain tumors, stroke, heart attack, meningitis, viral encephalitis, and other conditions that deprive the brain of oxygen. In a particular embodiment, the trauma is an external, physical force.

The damage can be focal (confined to one area of the brain) or diffuse (involving more than one area of the brain). Clinically, traumatic brain injury can be rated as mild, moderate or severe based on TBI variables that include duration of loss of consciousness (LOC), Glasgow Coma Score (GCS) and post traumatic stress amnesia (see, e.g., Levin et al. (1979) J. Nervous Mental Dis., 167:675-84; Holm et al. (2005) J. Rehabil. Med., 37:137-41).

In some embodiments, the traumatic brain injury can be chronic, where the brain is subject to repeated traumatic injury to the brain. Generally, chronic traumatic brain injury is typically a mild to moderate form of closed brain injury repeatedly suffered by a subject (e.g., athlete, combat soldier), resulting in increased incidence of impaired motor, cognitive, and/or behavioral impairments months to years following the traumatic brain injuring events. Individuals subjected to such chronic brain injury appear to have increased susceptibility to certain neurological disorders, such as Alzheimer's disease, and/or Parkinson's Disease.

In some embodiments, the traumatic brain injury can result from a closed head injury. The closed head injury may be transient or prolonged. A "closed head injury" refers to a brain injury when the head suddenly and violently hits an object but the object does not break through the skull. In some embodiments, the closed head injury is a concussion or contusion. A concussion is a mild form of traumatic brain injury resulting in temporary impairment of neurological function which quickly resolves by itself, and where there are generally no gross structural changes to the brain as the result of the condition. A contusion is a distinct area of swollen brain tissue mixed with blood released from broken blood vessels. A contusion can also occur in response to shaking of the brain back and forth within the confines of the skull, an injury referred to as "contrecoup." As used herein, a closed head injury refers to an injury due to an external, physical trauma and does not encompass brain injury resulting from "internal" forces such as ischemia/reperfusion and stroke.

Polymers

The instant invention provides copolymers, particularly N-(2-hydroxypropyl)methacrylamide (HPMA) copolymers, conjugated to at least one therapeutic agent and/or imaging agent. HPMA copolymers suitable for use in the instant invention and methods of synthesis the copolymers are described, for example, in U.S. patent application Ser. Nos. 10/591,258 and 127351,417 and PCT application PCT/US10/48231.

While HPMA copolymers are exemplified throughout the instant application, other polymer backbones or colloidal systems, particularly water soluble ones) may be used (see, e.g., PCT/US10/48231). The polymers may comprise (be conjugates to) at least one therapeutic agent and/or at least one imaging agent. In certain embodiments, the polymers of the complexes are block copolymers. Block copolymers are most simply defined as conjugates of at least two different polymer segments (Tirrel, M. In: Interactions of Surfactants with Polymers and Proteins. Goddard E. D. and Ananthapadmanabhan, K. P. (eds.), CRC Press, Boca Raton, Ann Arbor, London, Tokyo, pp. 59-122, 1992). The simplest block copolymer architecture contains two segments joined at their termini to give an A-B type diblock. Consequent conjugation of more than two segments by their termini yields A-B-A type triblock, A-B-A-B-type multiblock, multisegment A-B-C architectures, and the like. More complex architectures such as $(AB)_n$ or $A_nB_m$ starblocks which have more than two polymer segments linked to a single center, are also encompassed by the instant invention. Block sizes may be as described below (e.g., a block may comprise about 1 to about 1000 monomers, particularly about 10 to about 500).

Polymers of the instant invention include, but are not limited to, polymers comprising a methyl acrylamide backbone, HPMA copolymers and derivatives (e.g., HPMA-APMA copolymers), polyoxazolines (e.g., poly(2-oxazolines)), polyethylene glycol (PEG) (including branched or block copolymers, which may be degradable via peptide sequences, ester or disulfide bonds, etc.), polyglutamic acid, polyaspartic acid, vinyl polymers, acrylates, methyl acrylates, dextran, chitosan, cellulose and its derivatives, starch, gelatin, hyaluronic acid and its derivatives, and polymers or copolymers comprising at least one of the following monomers: N-isopropylacrylamide (e.g., PNIPAm), acrylamide, oxazoline, N,N-dimethylacrylamide, N-vinylpyrrolidone (e.g., PVP), vinyl acetate (e.g., resulting polymer hydrolyzed into polyvinyl alcohol or PVA), acrylates, methyl acrylates, hydroxyethylmethacrylate (e.g., PHEMA), 2-methacryloxyethyl glucoside, acrylic acid, methacrylic, vinyl phosphonic acid, styrene sulfonic acid, maleic acid, 2-methacrylloxyethyltrimethylammonium chloride, methacrylamidopropyltrimethyl-ammonium chloride, methacryloylcholine methyl sulfate, N-methylolacrylamide, 2-hydroxy-3-methacryloxypropyltrimethyl ammonium chloride, 2-methacryloxyethyl-trimethylammonium bromide, 2-vinyl-1-methylpyridinium bromide, 4-vinyl-1-methyl-pyridinium bromide, ethyleneimine, (N-acetyl)ethyleneimine, (N-hydroxyethyl)ethyleneimine and/or allylamine. The water-soluble polymer may be biologically inert or possess therapeutic activity. Colloidal systems/carriers include, without limitation, liposomes, nanoparticles, and micelles (optionally cross-linked).

In a particular embodiment of the instant invention, the polymers of the instant invention are copolymers comprising a methacrylamide backbone, wherein the methacrylamide units have alkyl or aryl side chains. In a particular embodiment, the amide (N) group of the methacrylamide backbone is omitted.

In another embodiment, the polymer of the instant invention has the general structure:

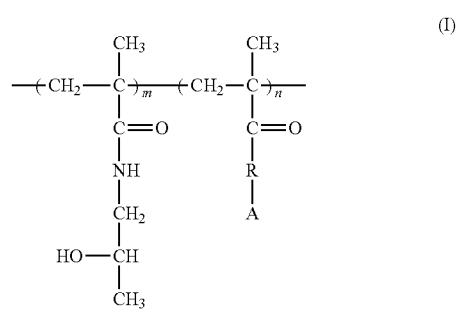

wherein R is a linker; A is an imaging agent or a therapeutic agent; and m and n are independently from about 1 to about 1000, particularly about 10 to about 500. In a particular embodiment, R is an alkyl, aryl, or polypeptide. In a particular embodiment, the R group comprises a pH sensitive linker and/or a cleavable linker. A single copolymer of the instant invention may comprise at least one imaging agent and/or at least one therapeutic agent. In other words, in the formulas provided herein, "A" need not be a single compound throughout the polymer and may represent at least one imaging agent, at least one therapeutic agent, or combinations thereof. For example, the "A" containing monomer may be distributed throughout the polymer (with different agents as the "A" group) and need not be present as a simple A-B copolymer (e.g., an A-B-A copolymer or an A-B-C copolymer).

In yet another embodiment, the polymer has the general structure:

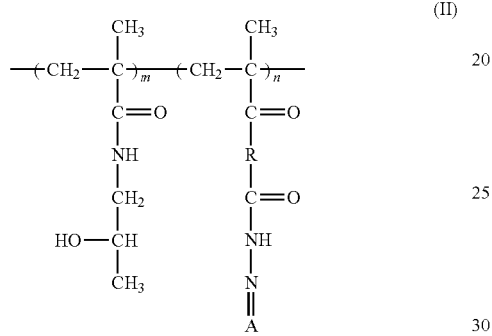

(II)

wherein R is a linker; A is a therapeutic agent or imaging agent; and m and n are independently from about 1 to about 1000, particularly about 10 to about 500. In a particular embodiment, R is an alkyl, aryl, or polypeptide. In another embodiment, the R group comprises a pH sensitive linker and/or a cleavable linker.

In still another embodiment, the polymer has the general structure:

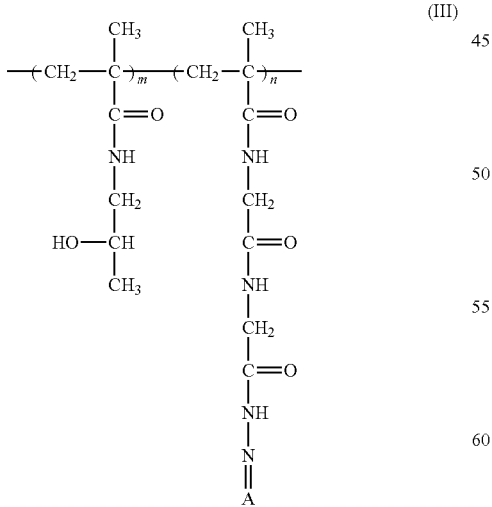

(III)

wherein A is a therapeutic agent; and m and n are independently from about 1 to about 1000, particularly about 10 to about 500.

In still another embodiment, the polymer has the structure:

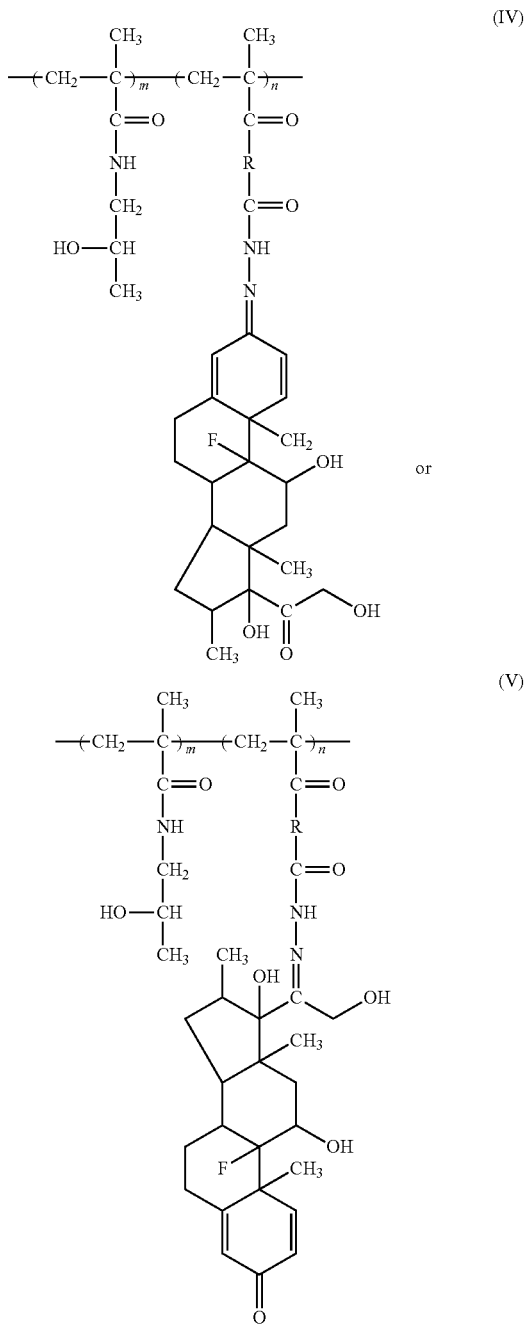

(IV)

or (V)

wherein R is a linker and m and n are independently from about 1 to about 1000, particularly about 10 to about 500. In a particular embodiment, R is an alkyl, aryl, or polypeptide. In another embodiment, the R group comprises a pH sensitive linker and/or a cleavable linker. In a particular embodiment, R (optionally including the preceding amine and the following carbonyl) is a polypeptide, particularly a glycine-glycine motif.

As stated hereinabove, the polymeric delivery systems of the instant invention can be used for the delivery of at least one therapeutic agent (drug) to the diseased sites for the treatment of TBI. In another embodiment, the delivery systems can be used for delivery of at least one imaging agent to the TBI sites for non-invasive imaging and evaluation of the TBI sites. The polymers of the instant invention may each comprise at least one therapeutic agent and/or imaging agent. In another embodiment, multiple polymers are administered (simultaneously or sequentially) each of which comprises different therapeutic agents and/or imaging agents.

Administration

The agents of the instant invention are used to treat, inhibit, reduce, and/or prevent the symptoms and/or pathology associated with traumatic brain injury (e.g., cognitive impairment, increased seizure rate) and will generally be administered to a patient as a pharmaceutical preparation. By providing early amelioration of trauma-induced brain inflammation, neurons and brain functions are protected. The term "patient" as used herein refers to human or animal subjects. The instant invention also encompasses compositions comprising at least one HPMA copolymer of the instant invention and at least one pharmaceutically acceptable carrier.

In a particular embodiment, the composition(s) of the instant invention are administered immediately or soon after the traumatic brain injury event. In a particular embodiment, the compositions of the instant invention are administered at least within about the first 7 days after injury, within 3 days after injury, within about the first day after injury, within about 12 hours after the injury, within about 6 hours after injury, within about 3 hours after the injury, or within about an hour after injury.

As used herein, a "therapeutically effective amount" of an agent or composition of the present invention is an amount sufficient to modulate pathology associated traumatic brain injury in a patient.

The compositions comprising at least one of the agents of the instant invention may be conveniently formulated for administration with a pharmaceutically acceptable carrier. Solubility limits of the agents within the particular pharmaceutically acceptable carrier may be easily determined by one skilled in the art.

Compositions of the instant invention may be administered by any method. For example, the compositions of the instant invention can be administered, without limitation, parenterally, subcutaneously, orally, topically, pulmonarily, intravenously, intraperitoneally, intrathecally, intracerbrally, epidurally, intramuscularly, intradermally, or intracarotidly. In a particular embodiment, the polymers of the instant invention are administered intravenously, intraperitoneally, or intramuscularly. In a particular embodiment, the polymers of the instant invention are administered intravenously. Pharmaceutical preparations for injection are known in the art. If injection is selected as a method for administering the polymer of the instant invention, steps should be taken to ensure that sufficient amounts of the molecules or cells reach their target cells to exert a biological effect.

In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., Tween 80, Polysorbate 80), anti oxidants (e.g., ascorbic acid, sodium metabisulfite), preservatives (e.g., Thimersol, benzyl alcohol) and bulking substances (e.g., lactose, mannitol). The pharmaceutical compositions of the present invention may be delivered in a controlled release system. The compositions can also be incorporated into particulate preparations of polymeric compounds such as polyesters, polyamino acids, hydrogels, polylactide/glycolide copolymers, ethyleneviny-lacetate copolymers, polylactic acid, polyglycolic acid, etc., or into liposomes. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized).

Pharmaceutical compositions containing agents of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous, oral, direct injection, or intracranial.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of compositions of the instant invention may be determined by evaluating the toxicity, if any, of the molecules or cells in animal models. Various concentrations of the agents in pharmaceutical preparations may be administered to mice, and the minimal and maximal dosages may be determined based on the beneficial results and side effects observed as a result of the treatment. Appropriate dosage unit may also be determined by assessing the efficacy of the treatment in combination with other standard drugs. The dosage units may be determined individually or in combination with each treatment according to the effect detected.

The compositions of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

In general, the compositions of the instant invention may contain other components in amounts that do not detract from the preparation of effective safe formulations. The compositions of the instant invention may further comprise at least one preservative, stabilizer, carriers, excipients, and/or antibiotic. Useful carriers for agents of the present invention may include, without limitation, any artificial or natural lipid-containing target molecule, cellular membranes, liposomes, and micelles. In a particular embodiment, compositions of the instant invention can be formulated as a liquid solution or suspension suitable for use with oral administration or syringes, infusion pumps (e.g., implantable pumps, intravenous pump), and cannulas. The compositions and methods of the instant invention may also be combined with other compositions and methods for the treatment of the symptoms and/or pathology of a traumatic brain injury.

The instant invention also encompasses compositions comprising at least one copolymer of the instant invention and at least one pharmaceutically acceptable carrier. The composition may further comprise at least one other anti-inflammatory therapeutic agent. Such composition may be administered, in a therapeutically effective amount, to a patient in need thereof for the treatment and/or imaging of TBI. In a particular embodiment, at least one other anti-inflammatory agent is administered separately from the above composition (e.g., sequentially or concurrently).

The composition of the instant invention may be administered for immediate relief of acute symptoms or may be administered regularly over a time course to treat and/or image the TBI. The dosage ranges for the administration of the composition of the invention are those large enough to produce the desired effect (e.g., curing, relieving, and/or preventing the TBI, the symptom of it, or the predisposition towards it). The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

Definitions

As used herein, "cognitive impairment" refers to an acquired deficit in at least one of the following: memory function, problem solving, orientation, and abstraction. The deficiency typically impinges on an individual's ability to function independently.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% or more by weight of the given compound. Purity is measured by methods appropriate for the given compound (e.g., chromatographic methods, agarose or polyacrylamide gel electrophoresis, HPLC analysis, and the like).

The term "prodrug" indicates a therapeutic agent that is prepared in an inactive or less active form that is converted to an active form (i.e., drug) within the body or cells thereof by the action of endogenous enzymes or other chemicals and/or conditions.

The term "isolated" refers to the separation of a compound from other components present during its production. "Isolated" is not meant to exclude artificial or synthetic mixtures with other compounds or materials, or the presence of impurities that do not substantially interfere with the fundamental activity, and that may be present, for example, due to incomplete purification, or the addition of stabilizers.

"Pharmaceutically acceptable" indicates approval by a regulatory agency of the Federal or a state government or listed in the U.S. Pharmacopeia or other generally recognized pharmacopeia for use in animals, and more particularly in humans.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions may be employed as carriers, particularly for injectable solutions. The compositions can be incorporated into particulate preparations of polymeric compounds such as polylactic acid, polyglycolic acid, etc., or into liposomes or micelles. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized). Suitable pharmaceutical carriers are described, for example, in Remington: The Science and Practice of Pharmacy, 21st Edition, (Lippincott, Williams and Wilkins), 2005; Pharmaceutical Dosage Forms, Liberman, et al., Eds., Informa Healthcare, 1989; and Handbook of Pharmaceutical Excipients (6th Ed.), Kibbe, et al., Eds., Pharmaceutical Pr, 2009.

The term "pathology" refers to any deviation from a healthy or normal condition, such as a disease, disorder, syndrome, or any abnormal medical condition.

"Linker", "linker domain", and "linkage" refer to a chemical moiety comprising a covalent bond or a chain of atoms that covalently attaches at least two compounds, for example, a targeting moiety to a therapeutic agent. The linker can be linked to any synthetically feasible position of the compounds, but preferably in such a manner as to avoid blocking the compounds desired activity. Linkers are generally known in the art. Exemplary linkers may comprise at least one optionally substituted; saturated or unsaturated; linear, branched or cyclic alkyl group or an optionally substituted aryl group. In a particular embodiment, the linker may contain from 0 (i.e., a bond) to about 500 atoms, about 1 to about 100 atoms, or about 1 to about 50 atoms. The linker may also be a polypeptide (e.g., from about 1 to about 20 amino acids). The linker may be biodegradable under physiological environments or conditions. The linker may also be may be non-degradable and can be a covalent bond or any other chemical structure which cannot be cleaved under physiological environments or conditions.

As used herein, the term "biodegradable" or "biodegradation" is defined as the conversion of materials into less complex intermediates or end products by solubilization hydrolysis under physiological conditions, or by the action of biologically formed entities which can be enzymes or other products of the organism. The term "non-degradable" refers to a chemical structure that cannot be cleaved under physiological condition, even with any external intervention. The term "degradable" refers to the ability of a chemical structure to be cleaved via physical (such as ultrasonication), chemical (such as pH of less than 6 or more than 8) or biological (enzymatic) means.

A "therapeutically effective amount" of a compound or a pharmaceutical composition refers to an amount effective to prevent, inhibit, lessen, or treat the symptoms of a particular disorder or disease.

The term "alkyl," as employed herein, includes linear, branched, and cyclic (see cycloalkyl below) chain hydrocarbons containing about 1 to about 20 carbons in the normal chain. An alkyl may be referred to as a hydrocarbyl. Examples of suitable alkyl groups include methyl, ethyl, propyl, isopropyl, butyl, t-butyl, isobutyl, pentyl, hexyl, isohexyl, heptyl, 4,4 dimethylpentyl, octyl, 2,2,4 trimethylpentyl, nonyl, decyl, the various branched chain isomers thereof, and the like. Each alkyl group may optionally be substituted (e.g., comprise 1 to about 4 substituents) with at least one substituent which include, for example, halo (such as F, Cl, Br, I), haloalkyl (such as $CCl_3$ or $CF_3$), alkyl, alkoxy, hydroxy, aryl, aryloxy, aralkyl, cycloalkyl, alkylamido, alkanoylamino, oxo, acyl, arylcarbonylamino, amino (—$NH_2$), substituted amino, nitro, cyano, carboxy (—COOH), carbonyl (—C(=O)), epoxy, urea (—$NHCONH_2$), thiol (—SH), alkylthio, alkyloxycarbonyl (—C(=O)—OR), alkylcarbonyloxy (—OC(=O)—R), carbamoyl ($NH_2C$(=O)— or NHRC(=O)—), and/or alkylurea (—NHCONHR), wherein R in the aforementioned substituents represents an alkyl radical. The alkyl group may optionally comprise one or more carbon to carbon double bonds (i.e., the alkyl group may be unsaturated). The alkyl may also comprise at least one (e.g., from 1 to about 4) sulfur, oxygen, or nitrogen heteroatoms within the hydrocarbon chain. For example, the alkyl can be —OR, —SR, or —NHR, wherein R is a hydrocarbon chain.

The term "cycloalkyl," as employed herein, includes saturated and/or unsaturated cyclic hydrocarbon groups containing 1 to 3 rings, that is, monocyclic alkyl, bicyclic alkyl and tricyclic alkyl. Cycloalkyl groups may contain a total of 3 to 20 carbons forming the ring(s), particularly 3 to 10 carbons forming the ring(s), and may optionally be fused to 1 or 2 aromatic rings as described for aryl, below. Unsaturated cycloalkyl groups may contain one or more double bonds and/or triple bonds. Cycloalkyl groups include, without limitation, cyclopropyl, cyclobutyl, cyclopentyl, cyclohexyl, cycloheptyl, cyclooctyl, cyclodecyl and cyclododecyl, cyclopentenyl, cyclohexenyl, cycloheptenyl, cyclooctenyl, cyclohexadienyl, and cycloheptadienyl. Each cycloalkyl group may be optionally substituted (e.g., comprise 1 to about 4 substituents) with substituents (see also above) such as halogen, alkyl, alkoxy, hydroxy, aryl, aryloxy, aralkyl, cycloalkyl, alkylamido, alkanoylamino, oxo, acyl, arylcarbonylamino, amino, substituted amino, nitro, cyano, thiol and/or alkylthio. The cycloalkyl may also comprise at least one (e.g., from 1 to about 4) sulfur, oxygen, or nitrogen heteroatoms within the hydrocarbon chain.

The term "aryl," as employed herein, refers to monocyclic and bicyclic aromatic groups containing 6 to 10 carbons in the ring portion. Examples of aryl groups include, without limitation, phenyl or naphthyl, such as 1-naphthyl and 2-naphthyl, or indenyl. Aryl groups may optionally include one to three additional rings fused to a cycloalkyl ring or a heterocyclic ring. Aryl groups may be optionally substituted through available carbon atoms with, for example, 1, 2, or 3 groups selected from hydrogen, halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocyclooxy, hydroxy, nitro, cyano, sulfonyl anion, amino, or substituted amino. The aryl group may be a heteroaryl. "Heteroaryl" refers to an optionally substituted, mono-, di-, tri-, or other multicyclic aromatic ring system that includes at least one, and preferably from 1 to about 4, sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

The terms "halogen," "halo," and "halide" particularly refer to chlorine, bromine, fluorine or iodine.

As used herein, the term "prevent", with regard to TBI, refers to the treatment of a subject who has sustained a TBI, but the treatment/therapy results in a decrease in the probability that the subject will develop the symptoms associated with TBI.

The following example is provided to illustrate various embodiments of the present invention. It is not intended to limit the invention in any way.

EXAMPLE

Figure 2:
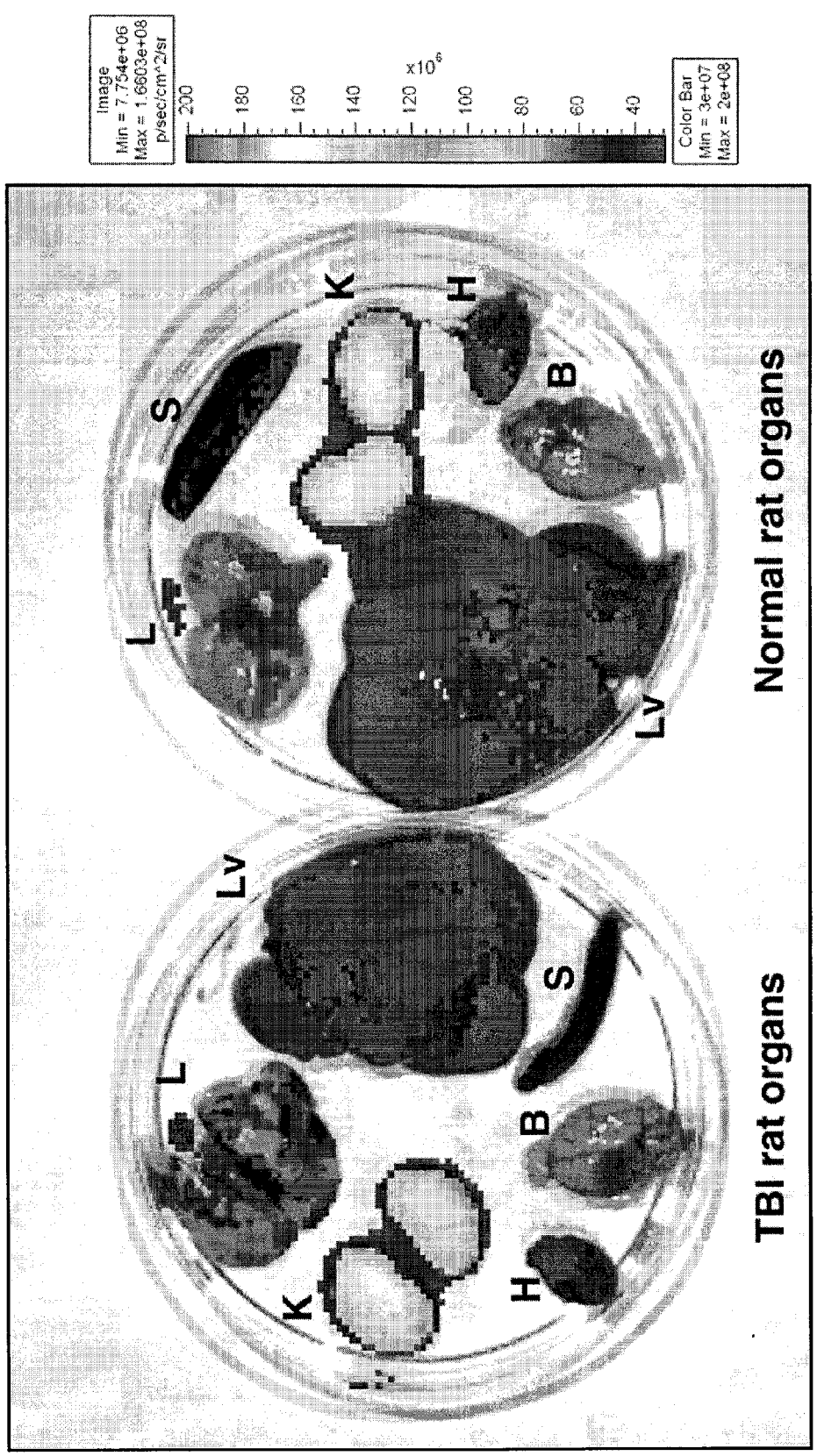
FIG. 2 provides images of organs from control rats or rats given a traumatic brain injury (TBI), after administration of near infrared dye labeled HPMA copolymers. H=heart; B=brain; S=spleen; K=kidneys; Lv=liver; L=lungs.

The targeting of the macromolecular prodrug of the instant invention to traumatic brain injury TBI sites was evaluated. Certain materials and methods are provided in Liu et al. (Pharm. Res. (2008) 25(12):2910-9). As shown in the following figures, after TBI, the i.v. administered near infrared (NIR) dye-labeled HPMA copolymer effectively accumulated at the injury site, while no such accumulation could be found in normal rats (FIG. 1, 5 hours post injection). The main clearance route of the HPMA copolymer based prodrug is the kidney, which is clearly evident in FIG. 2 (5 hours post injection).

The therapeutic efficacy of the macromolecular prodrug on TBI was also evaluated. For the efficacy study, the potent anti-inflammatory drug dexamethasone was conjugated to HPMA copolymer via an acid-cleavable hydrazone bond. As shown in the following figures, the prodrug (P-Dex), provides superior neuroprotection to the animals when compared to the equivalent dose free Dex. P-Dex was synthesized as described in Liu et al. (Pharm. Res. (2008) 25(12):2910-9).

Figure 3:
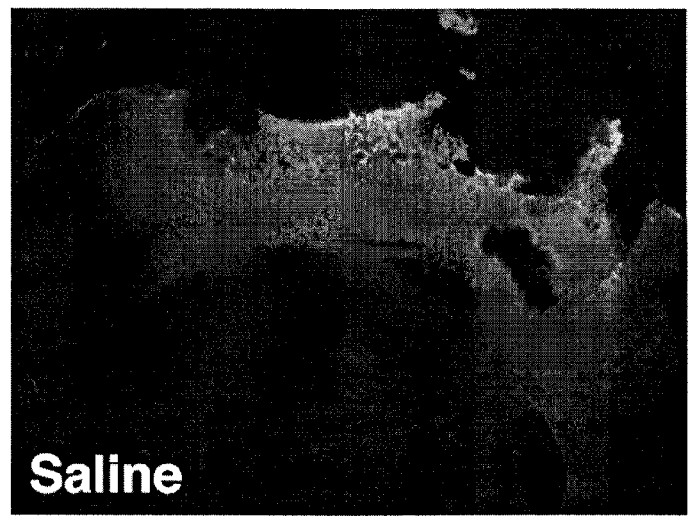
FIG. 3 provides representative photomicrographs of macrophage/microglia presence around the lesion site and hippocampus following traumatic brain injury (2 mm controlled cortical impact) in animals treated with saline, dexamethasone, or P-Dex.
Figure 3:
Figure 3:

FIG. 3 provides representative photomicrographs of macrophage/microglia presence around the lesion site and hippocampus following traumatic brain injury in animals treated with saline, dexamethasone (Hawkins, Inc., Minneapolis, Minn.) or P-Dex immediately following a 2 mm controlled cortical impact. Notably, there is less staining in the hippocampus, consistent with diaminobenzidine (DAB)-visualized images that were used for immunoreactivity quantification. Additionally, there is less staining in the cortex around the lesion site in the P-Dex treated animals compared to the dexamethasone and saline groups. These data indicate a superior anti-inflammatory and neuroprotective effect of P-Dex than dose equivalent Dex.

Figure 4:
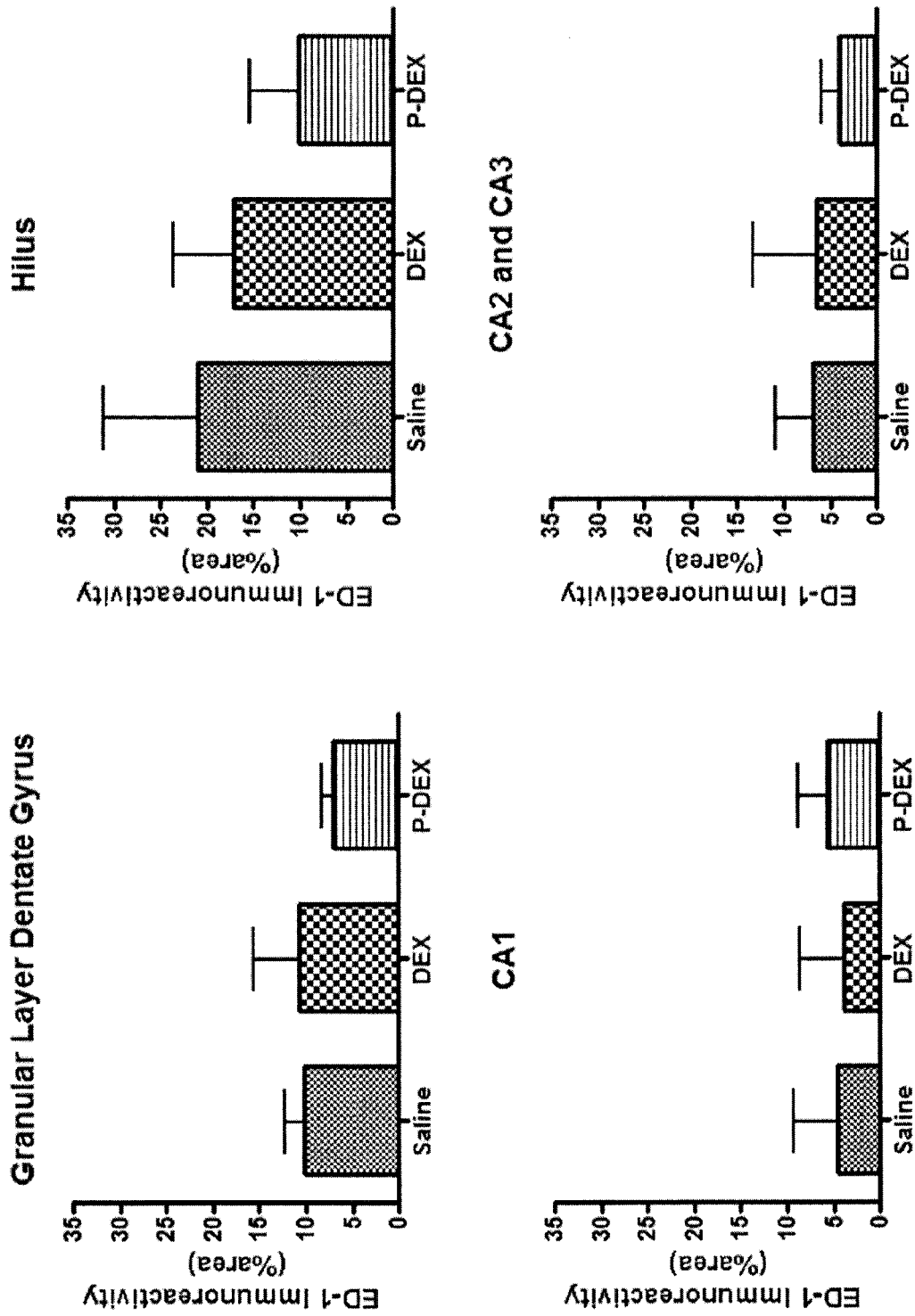
FIG. 4 provides graphs showing the quantification of ED-1 immunoreactivity in regions of the hippocampus following traumatic brain injury (2 mm controlled cortical impact) in animals treated with saline, dexamethasone, or P-Dex. Data are expressed as mean±standard deviation.

FIG. 4 provides quantified ED-1 immunoreactivity in regions of the hippocampus signifying macrophage/microglia presence. There is a significant reduction in ED-1 immunoreactivity in the CA2/3, granule cell layer, and hilar regions of the hippocampus for the P-Dex treatment group. Immunoreactivity was assessed by using free-floating rat brain sections that were incubated with a monoclonal anti-ED-1 antibody (1:800 dilution, AbD Serotec, Raleigh, N.C.). Primary Ab detection was performed using biotinylated antimouse secondary antibody enhanced with avidin-biotin complex (VECTASTAIN®, Vector Laboratories, Burlingame, Calif.) and DAB as the chromagen (Polysciences, Warrington, Pa.). Images of stained sections were collected on a Leica DM2500 microscope using a 2.5× objective and Leica EC3 camera. The images were converted to an 8-bit binary image and % area was quantified in the region of interest drawn by an evaluator blinded to the treatment groups.

Mice (9 adult male imprinting control region (ICR) mice) were subjected to a controlled cortical impact (CCI) model of traumatic brain injury (n=6) or sham injury (n=3) as previously described (Kelso et al. (2009) BMC Neurosci., 10:108; Kelso et al. (2006) Brain Res., 1083:204-10; Boulet et al. (2011) J. Neurosci. Methods 201:296-306). Briefly, the anesthesia was induced with 5% inhaled isoflurane. The animals had their heads shaved and were placed in a Kopf stereotaxic frame (Tujunga, Calif.) with 2% inhaled isoflurane delivered through a nosecose. A midline incision of the scalp was made and a unilateral craniotomy was performed lateral to the midline and between bregma and lambda taking care to leave the underlying dura undisturbed. The animals were placed beneath a Precision Systems and Instrumentation TBI-0310 that delivered a 0.5 mm cortical impact at 3.5 m/s with a dwell time of 500 msec. Following injury, Surgicel® (Johnson & Johnson, Dallas, Tex.) was placed over the craniotomy. The craniotomy was covered with a small disk of dental acrylic and the incision was sutured. Topical analgesia was provided by administration of 0.5% bupivacaine to the incision site. Sham injured animals had identical procedures performed except for the impact.

Figure 5:
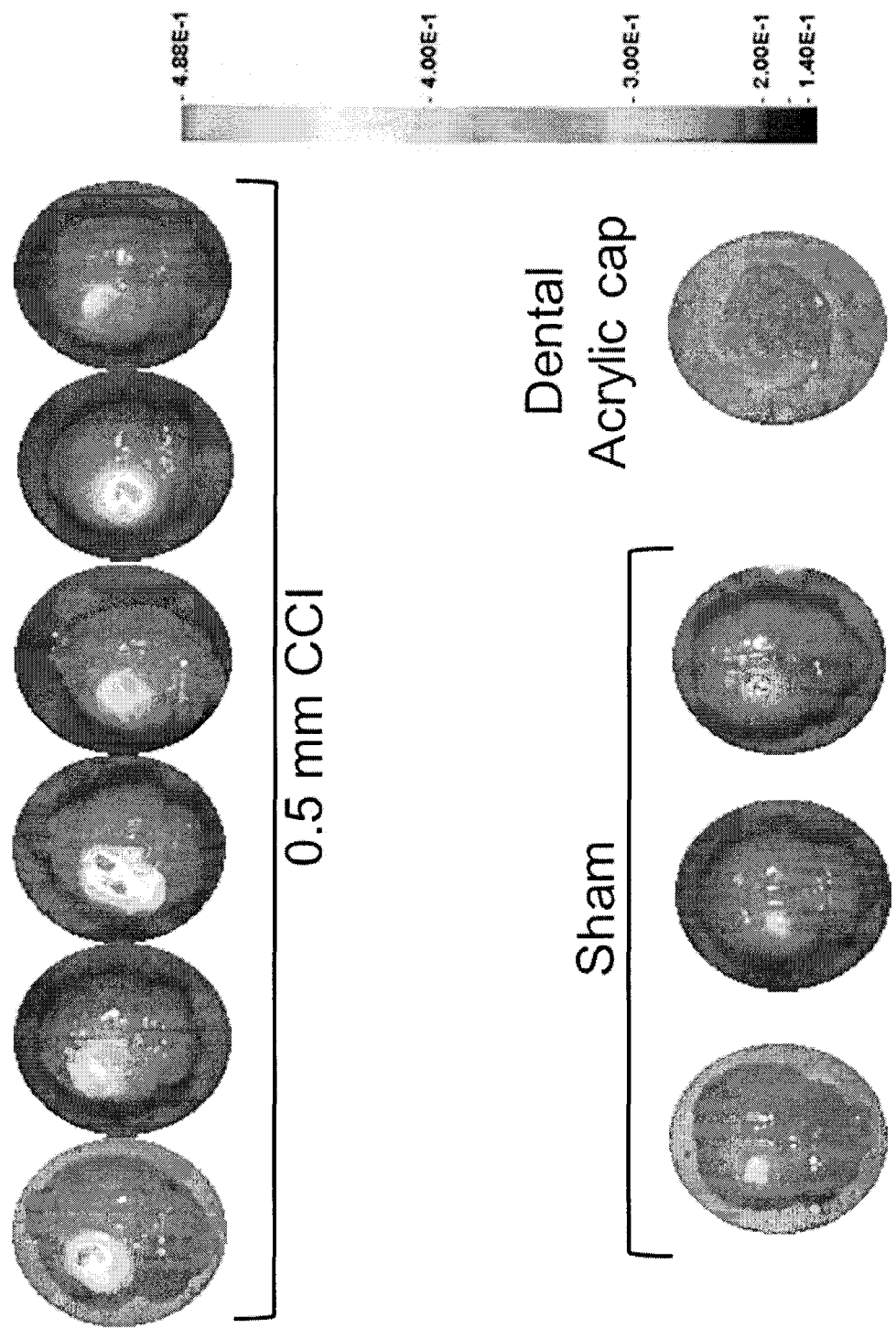
FIG. 5 provides images of mice brains administered a controlled cortical impact (CCI) or sham treated. Mice were administered HPMA conjugated to the IRDye 800W.

The animals were returned to their home cages and allowed to recover overnight. The following day, HPMA copolymer conjugate labeled with IRDye 800W was administered by tail vein injection. Two days later, the animals were anesthetized and rapidly decapitated with scissors. Brain tissue was harvested and imaged using Li-Cor Pearl™ imager. While it was observed that sham injury produced enough damage to cause drug accumulation around the craniotomy site, this accumulation was most likely due to the disruption of the skull for the craniotomy (Cole et al. (2011) J. Neurotrauma 28:359-69). Regardless, there was significantly more signal in the cortex of the CCI animals indicating higher drug accumulation (FIG. 5). Drug accumulation appeared limited to the injured cortex, with little or no signal observed in the subcortical structures.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for reducing in a subject the pathology associated with traumatic injury to the brain, wherein said subject has sustained a traumatic brain injury, said method comprising administering to the subject at least one polymer and at least one pharmaceutically acceptable carrier,
wherein said polymer comprises at least one anti-inflammatory agent conjugated to the polymer,
wherein said polymer is a N-(2-hydroxypropyl) methacrylamide (HPMA) copolymer having the structure:

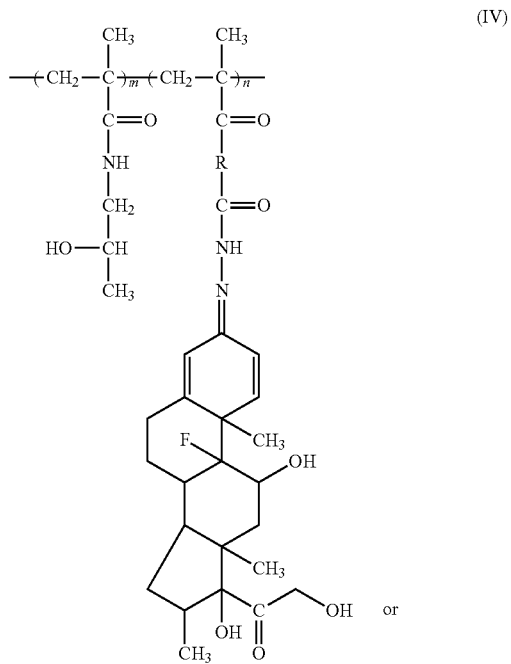

(IV)

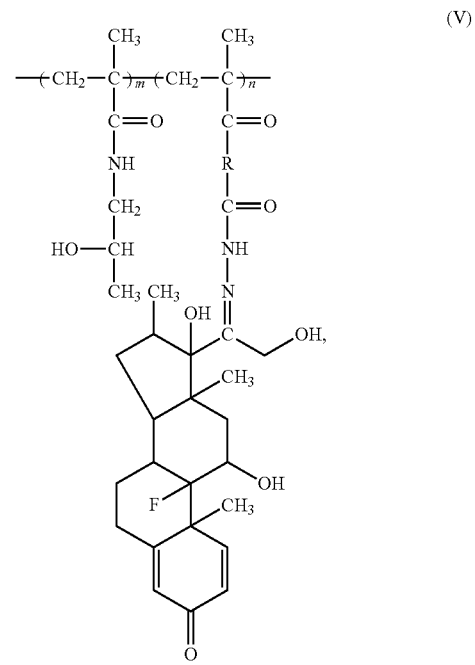

(V)

wherein m and n are independently from about 1 to about 1000, wherein R is a linker, and wherein said linker is an alkyl having one to about 15 carbons or a peptide having 1 to about 10 amino acids.

2. The method of claim 1, wherein said composition is administered to the subject within one day of the traumatic brain injury.

3. The method of claim 2, wherein said composition is administered to the subject within about 6 hours of the traumatic brain injury.

4. The method of claim 1, wherein said polymer further comprises at least one imaging agent.

5. The method of claim 1, wherein said composition is administered intravenously, intraperitoneally, or intramuscularly.

6. The method of claim 1, wherein said HPMA copolymer is

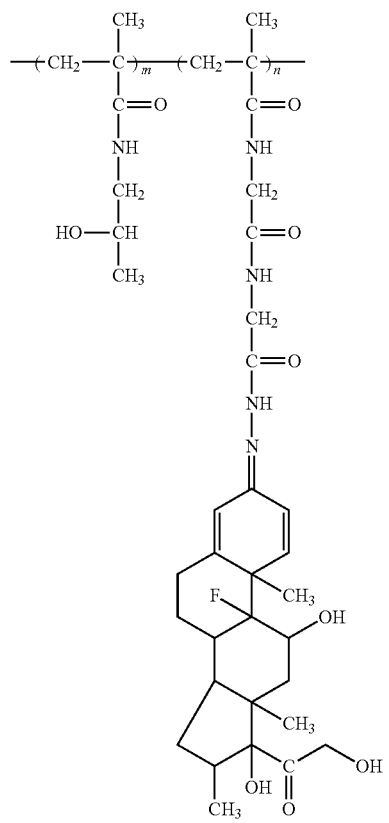

or

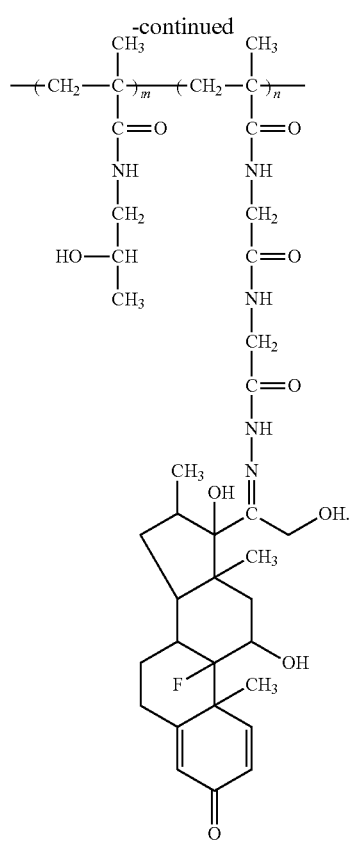

7. The method of claim 1 further comprising the administration of at least one additional anti-inflammatory agent.

8. The method of claim 1, wherein said composition is administered intravenously.

* * * * *